United States Patent
Schröder

(10) Patent No.: US 6,897,336 B2
(45) Date of Patent: May 24, 2005

(54) PREPARATION OF (METH)ACRYLIC ESTERS

(75) Inventor: Jürgen Schröder, Ludwigshafen (DE)

(73) Assignee: BASF Aktiengesellschaft, Ludwigshafen (DE)

(*) Notice: Subject to any disclaimer, the term of this patent is extended or adjusted under 35 U.S.C. 154(b) by 0 days.

(21) Appl. No.: 10/657,157

(22) Filed: Sep. 9, 2003

(65) Prior Publication Data

US 2004/0147772 A1 Jul. 29, 2004

(30) Foreign Application Priority Data

Jan. 17, 2003 (DE) ......................... 103 01 902

(51) Int. Cl.$^7$ .............................................. C07C 69/54
(52) U.S. Cl. ..................................................... 560/224
(58) Field of Search ....................................... 560/224

(56) References Cited

U.S. PATENT DOCUMENTS 5,554,785 A * 9/1996 Trapasso et al. ............ 560/201
6,175,037 B1 * 1/2001 Tweedy ...................... 560/224

FOREIGN PATENT DOCUMENTS

DE 10127941 * 5/2002
WO 2003042151 * 5/2003

OTHER PUBLICATIONS

Patent Abstracts of Japan, JP 2001–011018, Jan. 16, 2001.
L. B. Levy, et al., Process Safety Progress, vol. 12, No. 2, pp. 111–114, "Emergency Response Shortstop Inhibition During the Approach to an Acrylic Acid Runaway Polymerization", Apr. 1993.
J. J. Kurland, et al., Plant/Operations Progress, vol. 6, No. 4, pp. 203–207, "Shipboard Polymerization of Acrylic Acid", Oct. 1987.
L. B. Levy, Plant/Operations progress, vol. 6, No. 4, pp. 188–189, "Inhibitor–Oxygen Interactions in Acrylic Acid Stabilization", Oct. 1987.
L. B. Levy, Journal of Applied Polymer Science, vol. 60, pp. 2481–2487, "The Inhibition of Butyl Acrylate by P–Methoxyphenol", 1996.

* cited by examiner

*Primary Examiner*—Taofiq Solola
(74) *Attorney, Agent, or Firm*—Oblon, Spivak, McClelland, Maier & Neustadt, P.C.

(57) ABSTRACT

The present invention describes a process for preparing (meth)acrylic esters by acid-catalyzed esterification of (meth)acrylic acid or by transesterification of (meth)acrylic esters with alcohols, by adding the (meth)acrylic acid or the (meth)acrylic ester at a metering rate of less than 250 g per hour and liter of reactor volume and/or using at least 0.2 mmol of polymerization inhibitor per kg of alcohol and per meq/kg of peroxid number of the alcohol determined by the Sully method and/or thermally treating the alcohol in the absence of water before the esterification or transesterification.

11 Claims, No Drawings

PREPARATION OF (METH)ACRYLIC ESTERS

BACKGROUND OF THE INVENTION

1. Field of the Invention

The present invention describes a process for preparing (meth)acrylic esters by acid-catalyzed esterification of (meth)acrylic acid or by transesterification of (meth)acrylic esters.

2. Description of the Background

In this document, the term (meth)acrylic acid is an abbreviation of methacrylic acid and/or acrylic acid, and (meth)acrylic ester of methacrylic ester and/or acrylic ester.

The polymers and copolymers prepared based on (meth)acrylic esters are of great economic importance in the form of polymer dispersions. They find use, for example, as adhesives, paints or textile, leather and paper assistants.

(Meth)acrylic acid and (meth)acrylic ester are polymerizable compounds. Care therefore has to be taken in all process steps that there is sufficient polymerization inhibition. As a consequence of the large amounts of heat released, undesired polymerization is dangerous to safety. Examples of such runaway reactions are described, for example, in Process Safety Progress 1993, Vol. 12, 111–114 and Plant/Operations Progress 1987, Vol. 6, 203–207.

The preparation of (meth)acrylic esters in laboratory experiments is only reproducible to a limited extent. Some reactor charges polymerize unexpectedly. This effect occurs in particular when relatively old alcohols are used for the esterification or transesterification. Relatively old alcohols refer to alcohols which are not used directly after their preparation and are stored for an indefinite time, generally several days. These may contain peroxidic impurities which lead to the polymerization of (meth)acrylic acid or (meth)acrylic ester.

JP 2001/011018 describes the thermal treatment of cyclohexanol in the presence of water to remove peroxidic impurities. Subsequently, a cyclohexanol treated in this way is used for esterification or transesterification to cyclohexyl (meth)acrylates. A disadvantage of this process is that the alcohol contains water after the treatment. This has to be additionally removed in the course of the acid-catalyzed esterification. In the course of the transesterification, the catalysts used (for example titanium alkoxides) are destroyed by water.

In addition to the alcohols, (meth)acrylic acid is also capable of forming peroxides with atmospheric oxygen. This is especially significant because (meth)acrylic acid is blanketed with air in the course of storage for reasons of sufficient polymerization inhibition (Plan/Operations Progress 1987, Vol. 6, 188–189). For example, the peroxide number in acrylic acid stored for six months after HCl digestion is approx. 0.8 meq/kg (organic peroxide).

The situation is similar for (meth)acrylic ester also. As described by Levy in Journal of Applied Polymer Science 1996, Vol. 60, 2481–2487, organic peroxides are formed in the course of storage of butyl acrylate.

SUMMARY OF THE INVENTION

It is an object of the present invention to provide a process for preparing (meth)acrylic esters by esterifying (meth)acrylic acid or transesterifying (meth)acrylic esters with alcohols, which prevents or suppresses undesired polymerization.

We have found that this object is achieved by inhibiting the influence of the peroxidic impurities on the polymerization. This can be achieved by a) adding the (meth)acrylic acid or the (meth)acrylic ester at a metering rate of less than 250 g per hour and liter of reactor volume and/or b) using at least 0.2 mmol of polymerization inhibitor per kg of alcohol and per meq/kg of peroxid number of the alcohol determined by the Sully method.

A further embodiment includes the destruction of the peroxidic impurities in alcohols by c) thermally treating the alcohol in the absence of water before the esterification or transesterification.

DETAILED DESCRIPTION OF THE PREFERRED EMBODIMENTS

The process according to the invention relates preferably to esterifications or transesterifications with alcohols which may contain peroxidic impurities.

It will be appreciated that the peroxides may also be formed in the course of storage of (meth)acrylic acid or (meth)acrylic ester.

According to the invention, the (meth)acrylic acid or the (meth)acrylic ester is metered into the reactor at a rate of less than 250 g per hour and liter of reactor volume, preferably of less than 150 g per hour and liter of reactor volume, for example from 140 to 25 g per hour and liter of reactor volume, said reactor having been already initially charged with all other components such as alcohol, catalyst and polymerization inhibitors. It will be appreciated that the alcohol can also be added simultaneously with the (meth)acrylic acid or the (meth)acrylic ester.

In the present context, the reactor volume is the actual size of the reactor.

The esterification or transesterification takes place in at least one heatable reactor, in which suitable measures, for example stirring or circulation, ensure good mixing. When a plurality of reactors is used, for example from two to four, these may be arranged in a battery.

The reaction preferably takes place in a reactor.

The reactor is connected to at least one distillation unit which preferably has 30–50 theoretical plates.

Preference is given to the distillation unit being emplaced on the reactor.

It is also possible for a plurality of reactors to be connected to one distillation unit. The reflux from the distillation unit is then preferably recycled into the first reactor.

The distillation unit is of known design and has the customary internals. Useful column internals are in principle all common internals, for example trays, structured packings and/or random packings. Among the trays, preference is given to bubble-cap trays, sieve trays, valve trays, Thormann trays and/or dual-flow trays, and among the random packings, preference is given to those comprising rings, helices, saddles, Raschig, Intos or Pall rings, barrel or Intalox saddles, Top-Pak, etc., or braids.

The condenser, where present, is of conventional design.

In a preferred embodiment, the bottom region and the evaporator of a distillation unit are used as a reactor.

When the alcohol is fed in gaseous form, the preferred metering point is below the separating internals of the distillation unit or in the circulation circuit.

However, it is also possible for there to be one reaction zone which consists of one or more reaction sectors, for example a reactor battery of from two to four, preferably from two to three, reactors. Preference is given to using a reactor battery. When there is more than one reaction sector within one and the same reactor, for example by the use of dividing walls, the number of reaction sectors may also be more than four.

In a further embodiment of the process according to the invention, at least 0.2 mmol of polymerization inhibitor per kg of alcohol, preferably at least 0.5 mmol of polymerization inhibitor per kg of alcohol, per meq/kg of peroxide number of the alcohol is used.

In principle, hydroperoxides (I) and organic peroxides (II) may be present

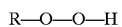
$$R\text{---}O\text{---}O\text{---}H \qquad (I)$$

$$R\text{---}O\text{---}O\text{---}R' \qquad (II).$$

Methods for quantitative detection of peroxides are described, for example, in Houben-Weyl, Methoden der organischen Chemie, 4th edition, volume 2, Analytische Chemie, pages 572–574. Organic peroxides which react slowly can only be detected with difficulty and have to be digested with strong acids.

For the determination of hydroperoxides, the glacial acetic acid-KI method (Rompp Chemie Lexikon, 9th edition, pages 3299 and 1341, and also Deutsche Einheitsmethoden zur Untersuchung von Fetten, Fettprodukten, Tensiden and verwandten Stoffen, C-VI 6a, Bestimmung der Peroxid-Zahl nach Sully) [German standard methods for investigating fats, fatty products, surfactants and related materials, C-V16a, Sully determination of the peroxide number]). For the determination of organic peroxides, the samples are preferably digested beforehand using hydrochloric acid.

The peroxide number is a measure of the content of peroxidically bound oxygen, in particular of hydroperoxides. It reports the number of millimoles of oxygen present in one kilogram of the sample which oxidize potassium iodide under the conditions of the method which follows and is reported in mmol of $O_2$ or in meq $O_2$/kg. To this end, the sample is reacted with potassium iodide in a mixture of chloroform and glacial acetic acid, and the iodine formed by the perodixe is determined titrimetrically. In the Sully method, the reaction described is effected in boiling solvent.

In a further embodiment c) of the process according to the invention, the alcohols are treated thermally in the absence of water immediately before their use as a reactant in the preparation of (meth)acrylic esters. This thermal treatment is effected in particular over a period of at least one hour, preferably at least two hours, at a temperature of at least 70° C., preferably at least 80° C.

In the absence of water means that the water content based on the entire mixture is less than 1% by weight, preferably less than 0.5% by weight and more preferably less than 0.3% by weight.

Typically, the alcohol is treated thermally in a tubular reactor, in a tank in which the alcohol is stirred or circulated, in a tank battery having at least two, preferably having from two to four, tanks, or a heated reservoir vessel.

The embodiments a) and b) of the process according to the invention mentioned find use individually, together and in combination with c).

In the process according to the invention, peroxide-containing alcohols are esterified and transesterified reliably with (meth)acrylic acid and (meth)acrylic esters respectively to give the corresponding (meth)acrylic esters.

It will be appreciated that the polymerization problems mentioned can also be limited when the alcohols intended for preparing (meth)acrylic esters are stored during preparation, storage in transport under a protective gas having less than 0.00015% by volume of oxygen, preferably having less than 0.000045% by volume of oxygen, based in each case on the total volume of the protective gas. The protective gas used may be noble gases such as argon, or nitrogen.

The alcohol used is typically any alcohol containing from 1 to 12 carbon atoms, for example mono- or polyhydric alcohols, preferably mono- to tetrahydric, more preferably mono- to trihydric, even more preferably mono- or dihydric and in particular monohydric.

Examples are methanol, ethanol, n-propanol, isopropanol, n-butanol, sec.-butanol, isobutanol, tert-butanol, ethylene glycol monomethyl ether, ethylene glycol monoethyl ether, diethylene glycol, 1,3-propanediol monomethyl ether, 1,2-propanediol, ethylene glycol, 2,2-dimethyl-1,2-ethanediol, 1,3-propanediol, 1,2-butanediol, 1,4-butanediol, dimethylaminoethanol, n-hexanol, n-heptanol, n-octanol, n-decanol, n-dodecanol, 2-ethylhexanol, 3-methylpentane-1,5-diol, 2-ethylhexane-1,3-diol, 2,4-diethyloctane-1,3-diol, 1,6-hexanediol, cyclopentanol, cyclohexanol, cyclooctanol, cyclododecanol, triethylene glycol, tetraethylene glycol, pentaethylene glycol, n-pentanol, stearyl alcohol, cetyl alcohol or lauryl alcohol, trimethylolbutane, trimethylolpropane, trimethylolethane, neopentyl glycol and the ethoxylated and propoxylated secondary products, neopentyl glycol hydroxypivalate, pentaerythritol, 2-ethyl-1,3-propanediol, 2-methyl-1,3-propanediol, 2-ethyl-1,3-hexanediol, glycerol, ditrimethylolpropane, dipentaerythritol, hydroquinone, bisphenol A, bisphenol F, bisphenol B, bisphenol S, 5-methyl-5-hydroxymethyl-1,3-dioxane, 2,2-bis(4-hydroxycyclohexyl)propane, 1,1-, 1,2-, 1,3- and 1,4-cyclohexanedimethanol, 1,2-, 1,3- or 1,4-cyclohexanediol.

Preferred alcohols are methanol, ethanol, n-butanol, isobutanol, sec-butanol, 2-ethylhexyl alcohol, n-octanol and dimethylaminoethanol. Very particular preference is given to methanol, ethanol, n-butanol, 2-ethylhexyl alcohol and dimethylaminoethanol.

It is also possible to use a plurality of alcohols, for example 2 or 3, but preference is given to using only one alcohol.

(Meth)acrylic esters are prepared in many cases in a manner known per se by esterifying (meth)acrylic acid with an alcohol, for example an alkanol. (Meth)acrylic esters are generally obtained via a homogeneously or heterogeneously catalyzed esterification, for example as described in Kirk Othmer, Encyclopedia of Chemical Technology, 4th Ed., 1994, pages 301–302 and Ullmann's Encyclopedia of Industrial Chemistry, 5th edition, volume A1, pages 167–169.

In the literature, numerous processes can be found for preparing (meth)acrylic esters by esterifying (meth)acrylic acid with an alcohol, for example in the German laid-open specifications DE 196 04 252 and DE 196 04 253. A process for preparing butyl acrylate by acid-catalyzed esterification of acrylic acid with butanol is described, for example, in WO 98/52904. An example of a batchwise acid-catalyzed esterification is EP 890 568.

The acidic catalysts which can be used are preferably sulfuric acid p-toluenesulfonic acid, benzenesulfonic acid, dodecylbenzenesulfonic acid, methanesulfonic acid or mixtures thereof, although acidic ion exchangers or zeolites are also conceivable.

Particular preference is given to using sulfuric acid, p-toluenesulfonic acid and methanesulfonic acid, very particular preference to sulfuric acid and p-toluenesulfonic acid.

The catalyst concentration based on the reaction mixture is, for example, from 1 to 20, preferably from 5 to 15% by weight.

The preparation of (meth)acrylic esters by transesterification in the presence of acidic or basic catalysts is generally known (Ullmann's Encyclopedia of Industrial Chemistry, 5th edition, volume A1, page 171).

In the literature, numerous examples can be found of transesterifications for preparing (meth)acrylic esters from (meth)acrylic esters with alcohols, for example the preparation of dimethylaminoethyl acrylate by transesterification of methyl acrylate with dimethylaminoethanol in EP 906 902. A batchwise transesterification is described, for example, in EP 1 078 913.

The catalysts proposed are in particular titanium alkoxides whose alkyl groups are $C_1$–$C_4$-alkyl radicals, for example, tetramethyl, tetraethyl, tetraisopropyl, tetrapropyl, tetraisobutyl and tetrabutyl titanate (see EP-B1 298 867, EP-A2 960 877). Further titanium compounds are also described in DE-A 10127939. Proposed catalysts also include titanium phenoxides (DE-A 200 86 18), dibutyltin oxide (EP-A 906 902), metal chelate compounds of, for example, hafnium, titanium, zirconium or calcium, alkali metal and magnesium alkoxides, organic tin compounds or calcium and lithium compounds, for example oxides, hydroxides, carbonates or halides.

Suitable stabilizers are in principle all polymerization inhibitors which are recommended for stabilizing (meth) acrylic acid and (meth)acrylic esters in DE-A 10258329.

Suitable stabilizers may, for example, be N-oxides (nitroxyl or N-oxyl radicals, i.e. compounds which have at least one >N—O group), e.g. 4-hydroxy-2,2,6,6-tetramethylpiperidine N-oxyl or 4-oxo-2,2,6,6-tetramethylpiperidine N-oxyl, phenols and naphthols such as p-aminophenol, p-nitrosophenol, 2-tert-butylphenol, 4-tert-butylphenol, 2,4-di-tert-butylphenol, 2-methyl-4-tert-butylphenol, 2,6-tert-butyl-4-methylphenol or 4-tert-butyl-2,6-dimethylphenol, quinones, e.g. hydroquinone or hydroquinone monomethyl ether, aromatic amines, e.g. N,N-diphenylamine, phenylenediamines, e.g. N,N'-dialkyl-p-phenylenediamine, where the alkyl radicals may be the same or different and may each independently consist of from 1 to 4 carbon atoms and be straight-chain or branched, e.g. N,N'-dimethyl-p-phenylene-diamine or N,N'-diethyl-p-phenylenediamine, hydroxylamines, e.g. N,N-diethyl-hydroxylamine, imines, e.g. methyl ethyl imine or methylene violet, sulfonamides, e.g. N-methyl-4-toluenesulfonamide or N-tert-butyl-4-toluenesulfonamide, oximes, such as aldoximes, ketoximes or amide oximes, e.g. diethyl ketoxime, methyl ethyl ketoxime or salicyladoxime, phosphorus compounds, e.g. triphenylphosphine, triphenyl phosphite or triethyl phosphite, sulfur compounds, e.g. diphenyl sulfide or phenothiazine, metal salts, e.g. cerium (III)acetate or cerium(III)ethylhexanoate, or mixtures thereof.

Preference is given to stabilizing with phenothiazine, hydroquinone, hydroquinone monomethyl ether, 4-hydroxy-2,2,6,6-tetramethylpiperidine N-oxyl, 4-oxo-2,2,6,6-tetramethylpiperidine N-oxyl, 2,6-tert-butyl-4-methylphenol or mixtures thereof.

Very particular preference is given to using phenothiazine as a polymerization inhibitor. The peroxide numbers in the examples which follow were determined by the glacial acetic acid-KI method (Römpp Chemie Lexikon, 9th edition, pages 3299 and 1341 and also Einheitsmethoden der Deutschen Gesellschaft für Fettwissenschaft, C-VI 6a, Bestimmung der Peroxid-Zahl nach Sully [Standard methods of the German Society for Fats Science, C-IV6a, Sully determination of the peroxide number]).

EXAMPLE 1

The peroxide numbers of various alcohols were determined. To this end, the alcohols were each heated to 100° C. in a stirred vessel for two hours. The stirred vessel was blanketed with nitrogen. Afterwards, 500 ml of the alcohol were transferred to a 1 l glass bottle under air. The alcohols were stored under air for 8 weeks.

| | |
|---|---|
| Methanol | 0.3 meq/kg |
| Ethanol | 0.3 meq/kg |
| n-Butanol | 0.6 meq/kg |
| 2-Ethylhexanol | 1.5 meq/kg |
| 5-Ethyl-5-hydroxymethyl-1,3-dioxane | 12.6 meq/kg |
| Tripropylene glycol | 2.3 meq/kg |
| 1,6-Hexanediol | 0.3 meq/kg |
| Triethoxylated trimethylolpropane | 7.4 meq/kg |
| Cyclohexanol | 163 meq/kg |

EXAMPLE 2

Preparation: Cyclohexanol was heated to 100° C. in a stirred vessel for two hours. The stirred vessel was blanketed with nitrogen. Afterwards, 500 ml of the thermally treated cyclohexanol were transferred to a 1 l glass bottle under air. The glass bottle was shaken vigorously once per day. After 7 days, the cyclohexanol pretreated in such a way was used. The peroxide number of the alcohol was 38 meq/kg.

Synthesis: A 1 liter four-necked flask equipped with a precision glass stirrer, thermometer, dropping funnel, and water separator was initially charged with 175 g of the pretreated cyclohexanol, 3.4 g of p-toluenesulfonic acid and 140 g of cyclohexane. The water separator was filled with cyclohexane. After 2 hours at 950° C., 165 g of methacrylic acid and 35 mg of phenotbiazine were added dropwise within approx. 2 minutes. The reaction temperature was increased to 120° C. by removing cyclohexane. Within 25 hours, a total of 75 g of aqueous phase was separated at a bottom temperature of 120° C.

The reaction mixture contained 1 mmol of phenothiazine per kg of alcohol, corresponding to 0.03 mmol of polymerization inhibitor per meq/kg of peroxide number of the alcohol.

The reactor contained no visible polymer.

EXAMPLE 3

The cyclohexanol was prepared as described in example 2. The peroxide number of the alcohol was 38 meq/kg.

Synthesis: A 1 liter four-necked flask equipped with a precision glass stirrer, thermometer, dropping funnel, and water separator was initially charged with 165 g of methacrylic acid, 175 g of the pretreated cyclohexanol, 3.4 g of p-toluenesulfonic acid, 630 mg of phenothiazine and 140 g of cyclohexane. The water separator was filled with cyclohexane. The reaction temperature was increased to 120° C. by removing cyclohexane. Within 25 hours, a total of 79 g of aqueous phase was separated at a bottom temperature of 120° C.

The reaction mixture contained 18 mmol of phenothiazine per kg of alcohol, corresponding to 0.47 mmol of polymerization inhibitor per meq/kg of peroxide number of the alcohol.

The reactor contained no visible polymer.

COMPARATIVE EXAMPLE 1

The cyclohexanol was prepared as described in example 2. The peroxide number of the alcohol was 43 meq/kg.

Synthesis: A 1 liter four-necked flask equipped with a precision glass stirrer, thermometer, dropping funnel, and water separator was initially charged with 165 g of methacrylic acid, 175 g of the pretreated cyclohexanol, 35 mg of phenothiazine, 3.4 g of p-toluenesulfonic acid and 140 g of cyclohexane. The water separator was filled with cyclohexane. The intention was to increase the reaction temperature to 120° C. by removing cyclohexane.

The reaction mixture contained 1 mmol of phenothiazine per kg of alcohol, corresponding to 0.02 mmol of polymerization inhibitor per meq/kg of peroxide number of the alcohol.

The reactor charge polymerized through on heating.

EXAMPLE 4

The cyclohexanol was prepared as described in example 2. The peroxide number of the alcohol was 43 meq/kg.

Synthesis: A 1 liter four-necked flask equipped with a precision glass stirrer, thermometer, dropping funnel, and water separator was initially charged with 175 g of the pretreated cyclohexanol, 3.4 g of p-toluenesulfonic acid and 140 g of cyclohexane and heated to 95° C. The reactor charge was heated up to within 30 minutes. On attainment of the reaction temperature of 95° C., the metered addition of the methacrylic acid was commenced immediately. The water separator was filled with cyclohexane. Within 2 hours, 165 g of methacrylic acid and 35 mg of phenothiazine were added dropwise. The reaction temperature was increased to 120° C. by removing cyclohexane. Within 25 hours, a total of 77 g of aqueous phase was removed at a bottom temperature of 120° C.

The reaction mixture contained 1 mmol of phenothiazine per kg of alcohol, corresponding to 0.02 mmol of polymerization inhibitor per meq/kg of peroxide number of the alcohol.

The metering rate was 83 g of methacrylic acid per hour and liter of reactor volume.

A negligibly small amount of polymer formed on the flask wall which caused no problems.

EXAMPLE 5

A 2 liter four-necked flask equipped with a precision glass stirrer, thermometer, dropping funnel and water separator was initially charged with 326 g of n-butanol, 12.8 g of 96 % sulfuric acid and 240 mg of hydrogen peroxide (30 % by weight in water). The water separator was filled with cyclohexane. After 2 hours at 95° C., 288 g of acrylic acid and 72 mg of phenothiazine were added dropwise within approx. 2 minutes. Within 3.5 hours, a total of 66 g of aqueous phase was separated at a bottom temperature of from 95 to 105° C. and a pressure of 500 mbar.

The peroxide number was 14 meq/kg of alcohol. The reaction mixture contained 1.1 mmol of phenothiazine per kg of alcohol, corresponding to 0.08 mmol of polymerization inhibitor per meq/kg of peroxide number of the alcohol.

The reactor contained no visible polymer.

EXAMPLE 6

A 2 liter four-necked flask equipped with a precision glass stirrer, thermometer, dropping funnel and water separator was initially charged with 288 g of acrylic acid, 326 g of n-butanol, 288 mg of phenothiazine, 12.8 g of 96 % sulfuric acid and 240 mg of hydrogen peroxide (30 % by weight in water). The water separator was filled with n- butanol. Within 4 hours, a total of 69 g of aqueous phase was separated at a bottom temperature of from 90 to 105° C. and a pressure of 500 mbar.

The peroxide number was 14 meq/kg of alcohol. The reaction mixture contained 4.4 mmol of phenothiazine per kg of alcohol, corresponding to 0.31 mmol of polymerization inhibitor per meq/kg of peroxide number of the alcohol.

The reactor contained no visible polymer.

COMPARATIVE EXAMPLE 2

A 2 l four-neck flask equipped with precision glass stirrer, thermometer, dropping funnel and water separator was initially charged with 288 g of acrylic acid, 326 g of n-butanol, 288 mg of phenothiazine, 12.8 g of 96% sulfuric acid and 240 mg of hydrogen peroxide (30% by weight in water) and heated to 95° C. The water separator was filled with n-butanol. The intention was to subsequently separate aqueous phase at 500 mbar.

The peroxide number was 14 meq/kg of alcohol. The reaction mixture contained 1.1 mmol of phenothiazine per kg of alcohol, corresponding to 0.08 mmol of polymerization inhibitor per meq/kg of peroxide number of the alcohol.

After 1 hour, the reactor charge polymerized through.

EXAMPLE 7

A 2 l four-neck flask equipped with precision glass stirrer, thermometer, dropping funnel and water separator was initially charged with 326 g of n-butanol, 12.8 g of 96% sulfuric acid and 240 mg of hydrogen peroxide (30% by weight in water) and heated to 95° C. The reactor charge was heated up within 30 minutes. On attainment of the reaction temperature of 95° C., the metered addition of the acrylic acid was commenced immediately. The water separator was filled with n-butanol. Within 2 hours, 288 g of acrylic acid and 72 mg of phenothiazine were added dropwise. At a bottom temperature of from 95 to 105° C. and a pressure of 500 mbar, 66 g of aqueous phase were separated within 2.5 hours.

The peroxide number was 14 meq/kg of alcohol. The reaction mixture contained 1.1 mmol of phenothiazine per kg of alcohol, corresponding to 0.08 mmol of polymerization inhibitor per meq/kg of peroxide number of the alcohol.

The metering rate was 72 g acrylic acid per hour and liter of reactor volume.

The reactor contained no visible polymer.

I claim:

1. A method of esterification or transesterification, comprising:

reacting (meth)acrylic acid with an alcohol or a (meth) acrylic acid ester with an alcohol, each in the presence of a catalyst, the esterification or transesterification reaction being conducted under conditions which at least suppress the polymerization of (meth)acrylate compounds by one of the following techniques:

a) thermally treating the alcohol reactant in the absence of water before the esterification or transesterification reaction and then formulating an esterification or transesterification reaction medium containing the heat treated alcohol and a polymerization inhibitor in an amount of at least 0.2 mmol per kg of heat treated alcohol and per meq/kg of the peroxide number of the alcohol determined by the Sully method; or b) thermally treating the alcohol reactant in the absence of water before the esterification or transesterification reaction and then conducting the esterification or transesterification reaction in a medium containing the heat treated alcohol; or c) thermally treating the alcohol reactant in the absence of water before the esterification or transesterification reaction and then metering the (meth)acrylic acid or (meth)acrylic ester reactant into a reactor at a rate of less than 250 g per hour and liter of reactor volume which contains reaction medium comprising the thermally treated alcohol; or d) metering the (meth)acrylic acid or (meth)acrylic ester reactant into a reactor at a rate of less than 250 g per hour and liter of reactor volume which contains a reaction medium; or e) metering the (meth)acrylic acid or (meth)acrylic ester reactant into a reactor at a rate of less than 250 g per hour and liter of reactor volume which contains a reaction medium comprising an alcohol and at least 0.2 mmol of polymerization inhibitor per kg of alcohol and per meq/kg of peroxide number of the alcohol determined by the Sully method; or f) thermally treating the alcohol reactant in the absence of water before the esterification or transesterification reaction, formulating an esterification or transesterification reaction medium containing the heat treated alcohol and a polymerization inhibitor in an amount of at least 0.2 mmol per kg of heat treated alcohol and per meq/kg of the peroxide number of the alcohol determined by the Sully method and then metering the (meth)acrylic acid or (meth)acrylic ester reactant into a reactor at a rate of less than 250 g per hour and liter of reactor volume.

2. The method as claimed in claim 1, wherein the peroxide number of the alcohol of method aspects a) and e) is at least 0.1 meq/kg.

3. The method as claimed in claim 1, wherein the alcohol reactant is a mono- or polyhydric alcohol.

4. The method as claimed in claim 3, wherein the alcohol reactant is methanol, ethanol, isopropanol, n-butanol, sec-butanol, isobutanol, tert-butanol, ethylene glycol monomethyl ether, ethylene glycol monoethyl ether, diethylene glycol, 1,3- propanediol monomethyl ether, 1,2-propanediol, ethylene glycol, 2,2-dimethyl-1,2-ethanediol, 1,3-propanediol, 1,2-butanediol, 1,4-butanediol, diinethylaminoethanol, n-hexanol, n-heptanol, n-octanol, n-decanol, n-dodecanol, 2-ethylhexanol, 3-methylpentane-1,5-diol, 2-ethylhexane-1,3-diol, 2,4-diethyloctane-1,3-diol, 1,6-hexanediol, cyclopentanol, cyclohexanol, cyclooctanol, cyclododecanol, triethylene glycol, tetraethylene glycol, pentaethylene glycol, n-pentanol, stearyl alcohol, cetyl alcohol, lauryl alcohol, trimethylolbutane, trimethylolpropane, trimethylolethane, neopentyl glycol and the ethoxylated and propoxylated secondary products thereof, neopentyl glycol hydroxypivalate, pentaerythritol, 2-ethyl-1,3-propanediol, 2-methyl-1,3-propanediol, 2-ethyl-1,3-hexanediol, glycerol, ditrimethylolpropane, dipentaerythritol, hydroquinone, bisphenol A, bisphenol F, bisphenol B, bisphenol S, 5-methyl-5-hydroxymethyl-1,3-dioxane, 2,2-bis(4-hydroxycyclohexyl)propane, 1,1-, 1,2-, 1,3- or 1,4-cyclohexanedimethanol, or 1,2-, 1,3- or 1,4-cyclohexanedimethanol.

5. The method as claimed in claim 4, wherein the alcohol reactant is methanol, ethanol, n-butanol, 2-ethylhexyl alcohol and/or dimethylaminoethanol.

6. The method as claimed in claim 1, wherein the polymerization inhibitor is a member selected from the group consisting of N-oxides, phenols, quinones, aromatic amines, hydroxylamines, imines, sulfonamides, oximes, phosphorus compounds, sulfur compounds, metal salts and mixtures thereof.

7. The method as claimed in claim 6, wherein the polymerization inhibitor is phenothiazine.

8. The method as claimed in claim 1, wherein the alcohol reactant contains less than 1% by wt water.

9. The method as claimed in claim 8, wherein the thermal treatment of the alcohol reactant is done at a temperature of at least 70° C. for at least one hour.

10. The method as claimed in claim 1, wherein the esterification reaction is conducted in the presence of an acid catalyst selected from the group consisting of sulfuric acid, p-toluenesulfonic acid, benzenesulfonic acid, dodecylbenzenesulfonic acid, methanesulfonic acid and mixtures thereof.

11. The method as claimed in claim 1, wherein the transesterification reaction is conducted in the presence of a catalyst of titanium oxide, titanium phenoxide, dibutyltin oxide, chelate compounds of hafnium, titanium, zirconium or calcium, alkali metal and magnesium oxides, organotin compounds or calcium or lithium compounds.

* * * * *